(12) United States Patent
Leon et al.

(10) Patent No.: US 7,005,142 B2
(45) Date of Patent: Feb. 28, 2006

(54) VETERINARY DELIVERY SYSTEMS AND METHODS OF DELIVERING EFFECTIVE AGENTS TO ANIMALS

(76) Inventors: Thomas Leon, 20 Audrey Ave., Oyster Bay, NY (US) 11771-1532; John Berggren, 20 Audrey Ave., Oyster Bay, NY (US) 11771-1532; Paul Gabel, 20 Audrey Ave., Oyster Bay, NY (US) 11771-1532; Daniel S. Leon, 20 Audrey Ave., Oyster Bay, NY (US) 11771-1532

(*) Notice: Subject to any disclaimer, the term of this patent is extended or adjusted under 35 U.S.C. 154(b) by 0 days.

(21) Appl. No.: 10/730,712

(22) Filed: Dec. 5, 2003

(65) Prior Publication Data

US 2004/0115253 A1 Jun. 17, 2004

Related U.S. Application Data

(63) Continuation of application No. 09/344,693, filed on Jun. 25, 1999, now abandoned.

(51) Int. Cl.
*A61K 9/70* (2006.01)

(52) U.S. Cl. ............ 424/484; 424/485; 424/486; 424/487; 424/488; 424/434; 424/435; 424/438; 424/422; 424/444; 424/405; 424/407

(58) Field of Classification Search ......... 424/400, 424/422, 434, 435, 438, 444, 484–488, 405, 424/407

See application file for complete search history.

(56) References Cited

U.S. PATENT DOCUMENTS 4,713,239 A * 12/1987 Babaian et al. .......... 424/78.24
5,110,605 A * 5/1992 Acharya .................. 424/487

FOREIGN PATENT DOCUMENTS

EP 000643963 A2 * 3/1995
WO WO8910740 * 11/1989

* cited by examiner

*Primary Examiner*—Neil S. Levy
(74) *Attorney, Agent, or Firm*—Galgano & Burke, LLP

(57) ABSTRACT

A veterinary delivery system in the form of a pliable film comprising at least one binder, at least one lubricant, at least one solvent for the binder and lubricant, and an effective amount of at least one effective agent. According to one embodiment, a flavorant is included in a pliable hydrophilic film in order to enhance oral acceptability by the animal. In other embodiments, the films preferably have a moisture content of about 2–15%, preferably about 3–7% by weight. The hydrophilic films most preferably have at least one effective agent distributed homogeneously throughout the film.

8 Claims, No Drawings

VETERINARY DELIVERY SYSTEMS AND METHODS OF DELIVERING EFFECTIVE AGENTS TO ANIMALS

This is a continuation of U.S. Ser. No. 09/344,693 filed Jun. 25, 1999 now abandoned.

BACKGROUND

The present invention is directed to veterinary care and, more particularly, to veterinary delivery systems and methods of delivering effective agents to animals.

Effective veterinary care is very important to animal owners as well as the rest of society. Many people own household pets, such as dogs and cats, and often become emotionally attached to those pets. Other animals, such as dogs used for police work and search and rescue operations, race horses, etc, each play a significant role in society. The proper and efficient veterinary care of these and other animals is very important.

The administration of pharmaceuticals, such as antibiotics, anti-inflammatory agents, anti-viral agents, vaccines and wormers, are important to the health of these animals. Typical methods of administering pharmaceuticals to animals include vascular injections, muscular injections and oral administration of liquids or pills. Disadvantages of these known pharmaceutical delivery methods include difficulty in administration, pain to the animals, difficulty in measuring the dosages when liquids or pills are added to animal feed, since, for example, some time a number of animals will share a common feed container and animals will sometimes try to spit out medicine.

It would therefore be desirable to provide a delivery system for effective agents which is easier to administer. It would also be desirable to provide veterinary delivery systems which have a higher dose delivery accuracy than previous feed-mixed delivery systems.

It would also be desirable to provide a veterinary pharmaceutical delivery systems that can be at least partially absorbed into the animals vascular system through mucous membranes while other portions are ingested.

It would also be desirable to provide methods for delivering agents effective in the care of animals which provide quick efficacy, are easier to store, have longer storage shelf lives and which are less prone to being spit out by the animal receiving the effective agent.

SUMMARY OF THE INVENTION

One aspect of the present invention comprises a veterinary delivery system in the form of a pliable hydrophilic film comprising at least one binder, at least one lubricant, at least one solvent for the binder and lubricant, and an effective amount of at least one effective agent. As used herein, the term "effective agent" is meant to include any compound which has an effect upon one or more health properties of the recipient animal. For example, effective agents include compounds which are therapeutically active and are designed to treat a symptom of the animal such as illness, bad breath, incontinence, or others discussed below. An effective agent can also comprise a compound having cosmetic effects which will change any visual aspect of the animal, such as an agent which is designed to provide a healthier coat. Other pharmaceuticals are also included such as pharmaceutical actives, and is not limited to prescription medicines.

According to another preferred embodiment of the present invention, at least one flavorant is also included in a pliable hydrophilic film in order to enhance oral acceptability by the animal.

According to another aspect of the present invention, films preferably have a moisture content of not greater than about 15% by weight and most preferably have moisture content of about 3–7% by weight. The hydrophilic films most preferably have at least one effective agent distributed homogeneously throughout the film.

The present invention also comprises methods of delivering effective agents wherein a tacky hydrophilic film comprising at least one effective agent is placed within the oral cavity of an animal.

These and other embodiments of the present invention are described in greater detail below.

DETAILED DESCRIPTION

The various aspects of the present invention relate to veterinary pharmaceutical delivery systems and methods of delivering effective agents to animals. As used herein, the term "animals" is meant to indicate mammals, and to exclude humans. The novel methods and delivery systems described herein utilize a pliable, preferably hydrophilic, film which contains an effective amount of at least one effective agent. The preferred films of the present invention advantageously become sufficiently sticky upon contact with the mucousal membrane or tongue of an animal such that the film adheres to the animal's tongue or mucousal membrane and generally is difficult to spit out or be dislodged. The films are sticky upon contact due to their hydrophilic nature and relatively low initial moisture content. In order to further enhance the retention of the delivery systems films by the animal, preferred embodiments of the present invention also advantageously comprise flavorants which are particularly adapted to be acceptable by the particular animal.

One embodiment of the present invention comprises a pliable film comprising at least one binding agent, at least one lubricant, a solvent for the binding agent and the lubricant, and an effective amount of at least one effective agent. The binding agent provides the structural integrity to the pliable film, either chemically or physically, and may comprise polyvinyl alcohol, methycelluloses such as hydroxypropyl methylcellulose (HPMC) or carboxymethylcellulose, gelatins, starches, either alone or in combination. The final film comprises up to about 95% by weight of the binding agent, and preferably about 40% to 90% by weight, more preferably about 50% to 75% by weight.

The lubricant can comprise one or more of glycerins, glycols such as propylene glycols, oils such as fish oils or vegetable oils, and combinations thereof. The lubricant of the final film should generally be not greater than about 45% by weight of the final film, preferably not greater than about 25%, more preferably about 2 to 15% and most preferably about 4 to 8% by weight. Unless otherwise stated in this application, all percentages are by weight and are expressed as a percentage of the final film.

In order to properly blend the binding agent and lubricant, a solvent such as water or an organic solvent such as ethanol is preferably employed. In the final film, the solvent preferably comprises about 2 to 15% by weight of solvent and most preferably about 3 to 7% by weight. If desired, more than one solvent can be used.

The effective agents of the present invention can comprise a wide range of therapeutic actives, cosmetic agents and other veterinary pharmaceuticals such an antibiotics, pain relievers, anti-inflammatory agents, anti-viral agents, vaccines, wormers, heart wormers, nutritional supplements, hypothyroidism medication, arthritis medication, incontinence medication, agents for the control of tartar and plaque, pain relievers, agents for treatment of bacterial diseases and coccidiosis, and combinations thereof. For example, the effective agents can comprise antibiotics such as sulfamethoxazole combined with trimethoprim (ditrim), penicillin, amoxicillin, ampicillin, cephalexin, metronidazole, hypothyroidism medication, such as levothyroxine, agents for treatment of bacterial diseases and coccidiosis such as sulfadimethoxine, pain relievers such as buffered aspirin and prednisone, arthritis medication such as glucosamine HCl, chondroitin sulfate extracts (shark cartilage), minerals-calcium, manganese, magnesium, ascorbic acid (vitamin C), wormers and heartwormers such as ivermectin, fenbendazole, milbemycin oxime, filaribits, parental pamoate, toluene, dichlorophene, piperazine, and agents for the control of tartar and plaque such as tetrasodium pryrophosphate. The amount of the active ingredient employed in the initial mixture will depend upon the desired dosage. According to preferred embodiments of the present invention, the effective agent is preferably homogeneously distributed throughout the film.

In order to enhance the acceptability of the delivery systems of the present invention, preferred embodiments comprise flavoring agents such as beef, chicken, liver, bacon, cheese, apple, smoke, fish, mint such as spearmint or peppermint, and combinations thereof and others.

Various embodiments of the present invention can also comprise fillers to modify the taste, texture, palpability, stickiness, aroma or roughage characteristics of the film. Fillers can be readily chosen and can include fillers such as cornmeal, cornstarch, potato starch, bone meal, corn syrup, wheat germ, brewers yeast, xanthan gum, carrageenan and combinations thereof.

It is also in the scope of the present invention to include preservatives such as methyl paraben, propylparaben, ethylenediamine-tetraacetic acid (EDTA), stearic acid, diazolidinyl urea, imdiazolidinyl urea, and combinations thereof in order to enhance shelf stability and minimize microbial growth from contamination.

The delivery systems of the present invention can advantageously be manufactured on a bulk scale. In order to achieve the desired concentration of effective agent in the dosage form, preferred embodiments are manufactured on a weight by weight concentration of the total product. While the following description utilizes water-soluble ingredients, based upon the solubility of the effective agent, the base can be formulated to be either water soluble or non-water soluble.

Compounding

Ingredients are individually weighed or otherwise measured. Some formulas require an emulsion to be formed, based on the solubility of the active or other ingredients. Some ingredients may need to be combined in a series of smaller tanks, prior to being added to a larger tank, again depending on solubility, temperature and mixing characteristics. The ingredients are mixed and/or heated accordingly until a homogeneous solution is achieved. Because certain ingredients will require heat to aid dissolution, the tanks can be heated to reduce mixing time and increase ingredient solubility. The bulk can be used hot or cooled based on viscosity and physical characteristics required for the next phase of manufacturing.

Distribution and/or Transfer Onto Belt

The second step involves the transfer of the bulk evenly and at the desired thickness onto a belt or sheet of material that will be passed into an oven or otherwise treated to remove the majority of the solvent, e.g. water, from the blend. The belt itself can be made of a number of different materials including stainless steel, teflon, aluminum, a high temperature chemical resistant polymer, or metal alloy among others. The belt's physical dimensions are based on the width of the bulk film roll desired, and the temperature of the oven. There are a number of ways to cast or spread a bulk solution onto the belt evenly and in a manner which advantageously free from bubbles and striations. The following are some of these methods. (1) The bulk can be pumped onto the belt and spread with a blade or brush type device into an even displacement. (2) The bulk can be pumped through a slot dye, with a controlled head pressure, e.g. from about 10–200 psi., onto the belt with dimensions that provide an even displacement of liquid bulk. (3) The bulk can be sprayed through a series of nozzles onto the belt. (4) The bulk can be spread thinly and evenly by mechanical means. (5) The bulk can be poured onto the belt and allowed to run or be blown by forced air to an even distribution. The conveyor type belt system is set to move the product at a controlled speed to achieve the desired drying of the product. For example, the belt can advance the product from 2 to 35 feet per minute depending on the moisture in the product, drying rate, and the desired thickness. The films of the present invention generally should have thicknesses not greater than about 0.05 inches, preferably not greater than about 0.025 inches, and most preferably about 0.0005 to about 0.010 of an inch.

Evaporation

The belt passes through an oven or other type environmental chamber at a controlled speed, humidity, ventilation, and temperature to eliminate enough of the solvent to produce a film of the desired consistency. To accomplish this, the belt speed and oven temperature is controlled to avoid any degradation of the components while eliminating enough solvent from the formulation to achieve the desired pliability of the finished film. The optimal conditions are typically between about 35° C. and 100° C. The result is sheets of film approximately the width of the belt and the desired thickness. This bulk film contains a known percentage of active drug product.

The physical dimensions of the finished product typically can range in size from about 10–80 millimeters square, depending on the size of the dose to be delivered. The films of the present invention can be larger, smaller or a different shape without departing from the scope of the present invention.

A person administering the dosage preferably places the film on or under the tongue, between the cheek or gum, or on the pallet of the animal where the film will advantageously adhere and begin to dissolve. As the film dissolves, the effective agent is released and absorbed through the mucous membrane in the mouth and/or the gastro-intestinal tract.

Another aspect of the present invention is a method of delivering an effective agent to an animal comprising the steps of a method of delivering an effective agent to an animal comprising the steps of providing a pliable film comprising at least one binder, at least one lubricant, at least one solvent for said binder and said lubricant, and an effective amount of at least one effective agent; and placing said film within the oral cavity of said animal, e.g. manually. These films are preferably hydrophilic.

According to a still further embodiment, the film is placed within the oral cavity of an animal by first placing the film on an insert device and then placing at least a portion of the insert device within the oral cavity of the animal. The film can be adhered to the tongue of the animal or to a mucous membrane in the oral cavity.

Another aspect of the present invention comprises a method of delivering an effective agent utilizing a film, most preferably a hydrophilic film into the oral cavity of an animal. Those skilled in the art will appreciate that the veterinary care provider may not wish to insert his hand into the oral cavity of certain animals. Therefore, according to another aspect of the present invention, a film of the present invention is placed on an insert device and a portion of that insert device is placed within the oral cavity of the animal. The insert device can comprise a wooden dowel, a plastic applicator, something edible, such as a carrot or other vegetable matter, a baked item such as a bread stick or pretzel, or can be forced via pressurized air through a hollow tube into the animal's oral cavity.

According to another embodiment of the present invention, a plurality of effective agents are provided within a single film. For example, according to one embodiment, one effective agent is preferably absorbed transbuccally at a faster rate than a second effective agent which is provided in that same film. For example, the second effective agent may have time-release properties which, when ingested, provide sustained release over some period of time.

What is claimed is:

1. A method of delivering an effective agent to an animal comprising the steps of:

providing a pliable film comprising at least one binder, at least one lubricant, at least one solvent for said binder and said lubricant, and an effective amount of at least one effective agent; and placing said film within the oral cavity of said animal by adhering said film to the tongue of said animal.

2. A method of delivery of an effective agent to an animal according to claim 1 wherein said step of providing a pliable film comprises providing a hydrophilic film.

3. A method of delivering an effective agent to an animal according to claim 1 wherein said step of placing said film within the oral cavity of an animal comprises placing said film on an insert device and placing at least a portion of said insert device within the oral cavity of said animal.

4. A method of delivering an effective agent to an animal according to claim 1 wherein said step of providing a film comprises providing a fil comprising a flavorant.

5. A method of delivering an effective agent to an animal according to claim 1 wherein said step of providing a film comprises providing a film having a moisture content not greater than about 15% by weight.

6. A method of delivering an effective agent to an animal according to claim 1 wherein said step of providing a film comprises providing a film having a moisture content of about 3%–7% by weight.

7. A method of delivering an effective agent to an animal according to claim 1 wherein said step of providing a film comprises providing a film having a moisture content of about 4%–6% by weight.

8. A method of delivering an effective agent to an animal according to claim 1 wherein said step of providing a film comprises providing a film having a moisture content of about 4.5%–5.5% by weight.

* * * * *